United States Patent
Sircar et al.

(10) Patent No.: US 7,375,128 B2
(45) Date of Patent: May 20, 2008

(54) INHIBITORS OF $\alpha_1 \beta_2$ INTEGRIN MEDIATED CELL ADHESION

(75) Inventors: Ila Sircar, San Diego, CA (US); Marshall Morningstar, Framingham, MA (US); Masatoshi Kakushima, Yokohama (JP); Hidefumi Kaji, Toda (JP); Takayuki Kawaguchi, Tokyo (JP); Toshiyuki Kume, Saitama (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 715 days.

(21) Appl. No.: 10/503,602

(22) PCT Filed: Feb. 6, 2003

(86) PCT No.: PCT/US03/03449

§ 371 (c)(1), (2), (4) Date: Aug. 5, 2004

(87) PCT Pub. No.: WO03/066636

PCT Pub. Date: Aug. 14, 2003

(65) Prior Publication Data

US 2005/0171174 A1    Aug. 4, 2005

Related U.S. Application Data

(60) Provisional application No. 60/354,309, filed on Feb. 7, 2002.

(51) Int. Cl.
A61K 31/407 (2006.01)
C07D 487/02 (2006.01)

(52) U.S. Cl. .................. 514/413; 548/453

(58) Field of Classification Search ............ 548/453; 514/413
See application file for complete search history.

(56) References Cited

FOREIGN PATENT DOCUMENTS

AU    A-82875/87    6/1988
WO    WO 98/39303 A1    9/1998
WO    WO 98/58947 A1    12/1998
WO    WO-01/30781 A    5/2001

OTHER PUBLICATIONS

Accession No. 2005:24021, CAPLUS abstract of JP 2005068145, Sircar, Ila et al, "Pharmaceutical compositions containing 1,3-diazobicyclo[3.3.0]octane-2,4-dione derivatives for prevention and treatment of LFA-1 (integrin aLb2)-mediated diseases."*
Bochner, B.S., "Adhesion Molecules in Allergic Disease" Marcel Decker, Inc., pp. 1-24. 1997.
Gahmberg, C.G., "Leukocyte Adhesion: CD11/CD18 Integrins and Intercellular Adhesion Molecules", Curr Opin Cell Biol., pp. 643-650, Oct. 1997..
Panes J., et al., "Leukocyte-Endothelial Cell Adhesion:Avenues for Therapeutic Intervention", Br J. Pharmacol, pp. 537-550, Feb. 1999.
Dustin, M.L., et al., "Induction by IL 1 and Interferon-Gamma: Tissue Distribution, Biochemistry, and Function of a Natural Adherence Molecule (ICAM-1)", J. Immunol, pp. 245-254, Jul. 1, 1986.
Wingren, A.G., et al., "T Cell Activation Pathways: B7, LFA-3, and ICAM-1 Shape Unique T cell Profiles", Crit. Rev. Immunol., pp. 235-253, 1995.

* cited by examiner

*Primary Examiner*—Kamal A. Saeed
*Assistant Examiner*—Janet L Coppins
(74) *Attorney, Agent, or Firm*—Birch, Stewart, Kolasch & Birch, LLP

(57) ABSTRACT

The present invention relates to a compound of formula (I): wherein R is hydrogen atom, hydroxyl group or carbamoyl group, and n is 1 or 2, or a pharmaceutically acceptable salt thereof.

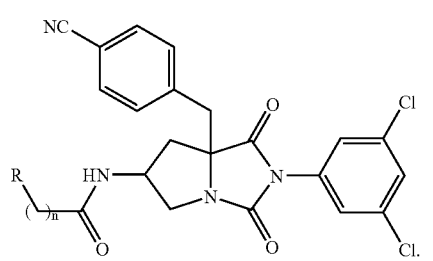

(I)

14 Claims, No Drawings

INHIBITORS OF $\alpha_L \beta_2$ INTEGRIN MEDIATED CELL ADHESION

This application is the national phase under 35 U.S.C. §371 of PCT International Application No. PCT/US03/03449 which has an International filing date of Feb. 6, 2003, for which priority is claimed under 35 U.S.C. §120. This application also claims priority to U.S. Provisional Application No. 60/354,309, filed Feb. 7, 2002, under 35 U.S.C. §119(e).

BACKGROUND OF THE INVENTION

1. Field of the Invention

The present invention relates to novel compounds that are potent inhibitors of $\alpha_L \beta_2$ integrin mediated cell adhesion which could be useful for the treatment of $\alpha_L \beta_2$ integrin mediated inflammatory conditions.

2. Description of Related Art

Leukocyte integrins and intercellular adhesion molecules (ICAMs) play pivotal roles in leukocyte adhesion to target cells and extracellular matrices. The $\beta_2$ (CD18) integrin subfamily has four members, each consisting of a related but distinct α-chain noncovalently paired with CD18: $\alpha_L \beta_2$ integrin (LFA-1, CD11a/CD18), $\alpha_M \beta_2$ integrin (Mac-1, CD11b/CD18), $\alpha_X \beta_2$ integrin (p150/95, CD11c/CD18), and $\alpha_D \beta_2$ integrin (CD11d/CD18) (Bochner ed., Adhesion Molecules in Allergic Disease, Marcel Dekker, Inc. pp 1-24 (1997)). Among them, LFA-1 has been shown to be central to the cell adhesion and transendothelial migration of T cells, eosinophils, and other leukocytes into inflamed tissues (Garmberg, Curr. Opin. Cell Biology, 9, 643-650 (1997); Panes et al., Br. J. Pharmacology, 126, 537-550 (1999)). LFA-1 binds to the ICAM family (ICAM-1, -2, -3, -4, -5) of molecules expressed on multiple cell types such as vascular endothelial cells, dendritic cells, epithelial cells, macrophage and T lymphoblasts (Dustin et al., J. Immunology, 137, 245-254 (1986)). In addition, LFA-1/ICAM-1 and LFA-1/ICAM-3 interactions can act as co-stimulatory signals required for T cell activation (Wingren et al., Crit. Rev. in Immunology, 15, 235-253 (1995)).

Cell migration and T cell co-activation are important processes in a number of inflammatory disease states. A dominant role of LFA-1 in mediating inflammatory events is shown in several different animal models of inflammatory diseases in which antibodies to LFA-1 or ICAM-1 significantly inhibit development of therapeutic end points (Rothlein et al., Kidney International, 41, 617 (1992); Iigo et al., J. Immunology, 147, 4167 (1991); Bennet et al., J. Pharmacol. and Exp. Therapeutics, 280, 988 (1997)). In addition, a humanized monoclonal antibody to CD11a (the alpha chain of LFA-1) has shown efficacy in patients with psoriasis (Gottlieb et al., J. Am. Acad. Dermatology, 42, 428-35 (2000)).

Moreover, it has been shown that antibodies against LFA-1 suppress rejection after organ transplantation (Poston et al., Transplantation 69, 2005-2013 (2000); Nakakura et al. Transplantation 62, 547-552 (1996)). WO 94/04188 discloses the use of monoclonal antibodies directed against $\alpha_L \beta_2$ integrin for all transplantations.

SUMMARY OF THE INVENTION

The present invention relates to novel compounds of formula (I):

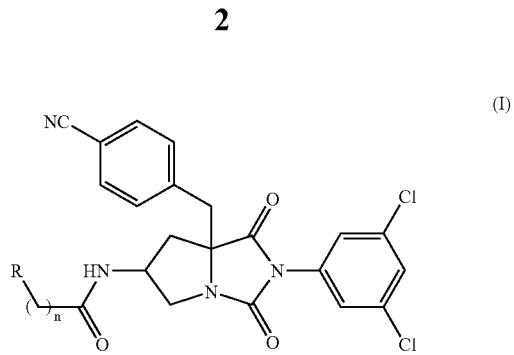

wherein R is hydrogen atom, hydroxyl group, or carbamoyl group, and n is 1 or 2, or a pharmaceutically acceptable salt thereof.

DETAILED DESCRIPTION OF THE INVENTION

The desired compounds of the present invention may exist in the form of optical isomers based on asymmetric atoms thereof, and the present invention also includes these optical isomers and mixtures thereof.

In an embodiment of the present invention, the steric configuration of a bond need not be fixed. The compounds of the present invention may be a compound with a sole configuration or a mixture with several different configurations.

In a preferred embodiment of the compounds of formula (I), R is hydrogen atom.

In another preferred embodiment of the compounds of formula (I), R is hydroxyl group.

In still another preferred embodiment of the compounds of formula (I), R is carbamoyl group.

In a more preferred embodiment of the compounds of formula (I), n is 1.

In another more preferred embodiment of the compounds of formula (I), n is 2.

In a further preferred embodiment of the compounds of formula (I), R is hydrogen atom and n is 1.

In another further preferred embodiment of the compounds of formula (I), R is hydroxyl group and n is 1.

In still another further preferred embodiment of the compounds of formula (I), R is carbamoyl group and n is 2.

Most preferred compounds of the present invention are selected from the following compounds:

(5S,7S)-5-(4-Cyanobenzyl)-3-(3,5-dichlorophenyl)-7-acetylamino-1,3-diazabicyclo[3.3.0]octane-2,4-dione;

(5S,7S)-5-(4-Cyanobenzyl)-3-(3,5-dichlorophenyl)-7-[(2-hydroxyacetyl)amino]-1,3-diazabicyclo[3.3.0]octane-2,4-dione;

(5S,7S)-5-(4-Cyanobenzyl)-3-(3,5-dichlorophenyl)-7-[(3-carbamoylpropionyl)amino]-1,3-diazabicyclo[3.3.0]octane-2,4-dione.

The characteristic of the present compounds is the combination of the acylamino group at 7-position and the 4-cyanobenzyl group at 5-position of 1,3-diazabicyclo[3.3.0]octane nucleus, where such characteristic is not specifically described in prior publications.

The compounds of the present invention have potent inhibitory activity against both LFA-1 mediated cell adhesion and LFA-1 mediated T cell co-activation, and also show excellent bioavailability after oral administration which reflects the overall improvement in (a) plasma protein binding, (b) aqueous solubility and (c) lipophilicity. The compounds of the present invention therefore show excellent in vivo efficacy against the unfavorable conditions caused by LFA-1 mediated cell adhesion.

In addition, the compounds of the present invention have potent antagonistic activity on substance P receptor, i.e., Neurokinin 1 (NK1) receptor, as well. Substance P receptor antagonists are considered to be useful for the treatment of inflammatory diseases such as asthma, rheumatoid arthritis, inflammatory bowel disease, cystitis, and other gastric disorders (Kraneveld et al., Int. Immunopharmacology, 1, 1629-1650 (2001); Swain et al., Ann. Rep. Med. Chem., 34, 51-60 (1999); Ohnmacht Jr. et al., Ann. Rep. Med. Chem., 33, 71-80 (1998)). Thus the compounds of the present invention has excellent therapeutic potential against the unfavorable conditions caused or mediated by substance P. Also, the compounds of the present invention may show excellent effects on the treatment or prevention of inflammatory diseases due to the dual activities of LFA-1 mediated cell adhesion inhibition and substance P receptor antagonism.

Moreover, the compounds of formula (I) have reduced cytotoxicity and low cytochrome P450 inhibitory activity as compared with those described previously, and therefore, the compounds of the present invention may have reduced side effect potential.

The compounds of the present invention may be clinically used either in a free form or in the form of pharmaceutically acceptable salts thereof. Pharmaceutically acceptable salts include an acid-addition salt with an inorganic acid or an organic acid, and a salt with an inorganic base, an organic base or an amino acid. Pharmaceutically acceptable salts also include an intramolecular salt thereof, or a solvate or hydrate thereof.

The compounds of the present invention may be formulated into a pharmaceutical composition comprising a therapeutically effective amount of the compound as defined above and a pharmaceutically acceptable carrier or diluent. The pharmaceutically acceptable carrier or diluent may be, for example, binders (e.g., syrup, gum arabic, gelatin, sorbitol, tragacanth, polyvinylpyrrolidone), excipients (e.g., lactose, sucrose, corn starch, potassium phosphate, sorbitol, glycine), lubricants (e.g., magnesium stearate, talc, polyethylene glycol, silica) disintegrators (e.g., potato starch), wetting agents (e.g., sodium laurylsulfate), and the like.

The desired compounds of the present invention or pharmaceutically acceptable salts thereof may be administered either orally or parenterally, and it may be used as a suitable pharmaceutical preparation. These pharmaceutical preparations may be in the form of a solid preparation such as a tablet, a granule, a capsule, and a powder, or in the form of a liquid preparation such as solution, suspension, and emulsion, when administered orally. When administered parenterally, the pharmaceutical preparation may be in the form of suppository, an injection preparation or an intravenous drip preparation using distilled water for injection, a physiological salt solution, an aqueous glucose solution, and so on, and an inhalation by a conventional process.

The dose of the desired compounds of the present invention or pharmaceutically acceptable salts thereof vary depending on an administration method, age, sex, body weight, and condition of a patient, but, in general, the daily dose is preferably about 0.1 to 100 mg/kg/day, particularly preferably 1 to 100 mg/kg/day.

The compounds of the present invention can be used for treating or preventing LFA-1 mediated conditions in a patient, for example, a human patient. The compounds of the present invention can be also used for the treatment of a patient suffering from or susceptible to LFA-1 mediated conditions. Examples of LFA-1 mediated conditions include inflammatory diseases, autoimmune diseases, and allergic diseases.

The compounds of the present invention can also be used for the treatment or prevention of conditions caused or mediated by substance P in a patient, as well as for the treatment of a patient suffering from or susceptible to such conditions. Examples of the conditions may be inflammatory diseases.

The compounds of the present invention may be used for treatment or prevention of diseases such as rheumatoid arthritis, asthma, chronic obstructive pulmonary disease, allergy conditions, adult respiratory distress syndrome, AIDS, cardiovascular diseases, thrombosis, harmful platelet aggregation, reocclusion following thrombolysis, reperfusion injury, skin inflammatory diseases (e.g., psoriasis, eczema, contact dermatitis, atopic dermatitis), osteoporosis, osteoarthritis, atherosclerosis, arteriosclerosis including transplantation-associated arteriosclerosis, neoplastic diseases including metastasis of neoplastic or cancerous growth, wound, detaching retina, Type I diabetes, multiple sclerosis, systemic lupus erythematosus (SLE), ophthalmic inflammatory conditions, inflammatory bowel diseases (Crohn's disease and ulcerative colitis), cystitis, gastric disorder, regional enteritis, Sjogren's Syndrome, and other autoimmune diseases.

The compounds of the present invention may also be used for the rejection (i.e., chronic rejection and acute ejection) after organ transplantation, including allograft rejection (host vs. graft disease) and graft vs. host disease.

The compounds of the present invention may be preferably used for treatment or prevention of psoriasis, rheumatoid arthritis, inflammatory bowel diseases (Crohn's disease, ulcerative colitis), systemic lupus erythematosus, atopic dermatitis, Sjogren's syndrome, and rejection after organ transplantation (allograft rejection and graft vs. host disease).

The compounds of the present invention may be further preferably used for treatment or prevention of rheumatoid arthritis, asthma, chronic obstructive pulmonary disease, psoriasis, multiple sclerosis, and rejection after organ transplantation.

The compounds of the present invention may also be further preferably used for treatment or prevention of inflammatory diseases such as asthma, inflammatory bowel disease, cystitis and other gastric disorders.

According to the present invention, the desired compounds (I) can be prepared in accordance with one of the following methods:

Method A:

Among the compounds of the present invention, a compound of formula (I-a):

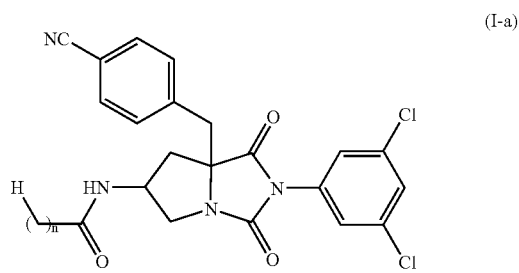

(I-a)

wherein n is the same as defined above, or a pharmaceutically acceptable salt thereof, can be prepared by condensing a compound of formula (II):

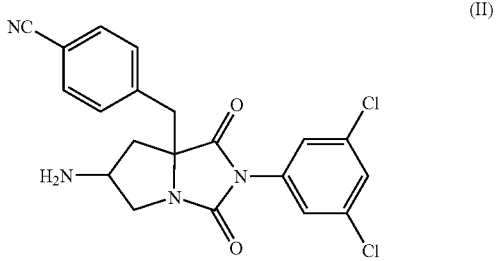
(II)

or a salt thereof, with a compound of formula (III-a):

(III-a)

wherein n is the same as defined above, a salt thereof, or a reactive derivative thereof, followed by converting the resulting compound into a pharmaceutically acceptable salt thereof, if desired.

The salt of compounds (II) and (III-a) may be, for example, a salt with an inorganic or organic acid (e.g., trifluoroacetate, hydrochloride, sulfate), or a salt with an inorganic base (e.g., an alkali metal salt such as a sodium salt or a potassium salt, an alkaline earth metal salt such as a barium salt or calcium salt).

The condensation reaction of the compound (II) or a salt thereof with the compound (III-a) or a salt thereof can be carried out in the presence of a condensing reagent, with or without a base in a suitable solvent.

The condensing reagent can be selected from conventional condensing reagents which can be used for a peptide synthesis, for example, BOP-Cl, BOP reagent, DCC, EDC or CDI. The condensing reagent can be preferably used with an activator (e.g., HOBT).

The base can be selected from conventional organic bases such as an alkylamine (e.g., DIEA, Et$_3$N), a cyclic amine (e.g., DBU, DBN, 4-methylmorpholine), and pyridines (e.g., pyridine, DMAP), and conventional inorganic bases such as an alkali metal carbonate (e.g., Na$_2$CO$_3$, K$_2$CO$_3$), an alkali metal hydrogen carbonate (e.g., NaHCO$_3$, KHCO$_3$), an alkali metal hydroxide (e.g., NaOH, KOH), and the like.

The solvent can be selected from any one which does not disturb the condensation reaction, for example, esters (e.g., methyl acetate, ethyl acetate), halogenoalkanes (e.g., CHCl$_3$, CH$_2$Cl$_2$), ethers (e.g., diethyl ether, THF, DME, dioxane), amides (e.g., DMF, N-methylpyrrolidone), ketones (e.g., acetone, methyl ethyl ketone), CH$_3$CN, DMSO, and H$_2$O, and a mixture of these solvents. The reaction can be carried out at a temperature of −50° C. to 50° C., preferably from 0° C. to room temperature.

The condensation reaction of compound (II) or a salt thereof with the reactive derivative of compound (III-a) is carried out in the presence or absence of a base in a suitable solvent or without solvent.

Examples of the reactive derivative of the compound (III-a) are an acid halide (e.g., an acid chloride), a reactive ester (e.g., an ester with p-nitrophenol), an anhydride thereof, a mixed anhydride with other carboxylic acid (e.g., a mixed anhydride with isobutyric acid), and the like.

The base can be selected from conventional organic bases such as an alkylamine (e.g., DIEA, Et$_3$N), a cyclic amine (e.g., DBU, DBN, 4-methylmorpholine), and pyridines (e.g., pyridine, DMAP), and conventional inorganic bases such as an alkali metal carbonate (e.g., Na$_2$CO$_3$, K$_2$CO$_3$), an alkali metal hydrogen carbonate (e.g., NaHCO$_3$, KHCO$_3$), an alkali metal hydroxide (e.g., NaOH, KOH), and the like.

The solvent can be selected from any one which does not disturb the condensation reaction, for example, esters (e.g., methyl acetate, ethyl acetate), halogenoalkanes (e.g., CHCl$_3$, CH$_2$Cl$_2$), ethers (e.g., diethyl ether, THF, dioxane), amides (e.g., DMF, N-methylpyrrolidone), ketones (e.g., acetone, methyl ethyl ketone), CH$_3$CN, DMSO, and H$_2$O, and a mixture of these solvents.

The condensation reaction can be carried out at a temperature of −30° C. to room temperature.

Method B:

Among the compounds of the present invention, a compound of formula (I-b):

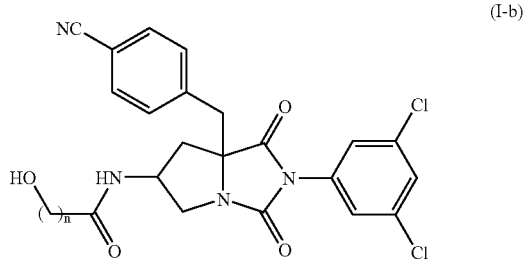
(I-b)

wherein n is the same as defined above, or a pharmaceutically acceptable salt thereof, can be prepared by condensing compound (II) or a salt thereof with a compound of formula (III-b):

(III-b)

wherein R$^1$O is a protected or unprotected hydroxyl group, and n is the same as defined above, a salt thereof, or a reactive derivative thereof, followed by removing the protecting group, and further converting the resulting compound into a pharmaceutically acceptable salt thereof, if necessary.

The salt of compound (III-b) may be, for example, a salt with an inorganic base (e.g., an alkali metal salt such as a sodium salt and a potassium salt, and an alkaline earth metal salt such as a barium salt and a calcium salt).

The protecting group for the hydroxyl group can be selected from conventional protecting groups for a hydroxyl group which can be easily removed by a conventional method. Examples of such protecting groups include a trialkylsilyl group (e.g., trimethylsilyl group, triethylsilyl group, and t-butyldimethylsilyl group), a benzyl group, a methyl group and a tetrahydropyranyl group.

The condensation reaction of compound (II) or a salt thereof with compound (III-b) wherein R$^1$O is a protected hydroxyl group, a salt thereof or a reactive derivative thereof can be carried out in a similar procedure as described in Method A.

The removal of the protecting group can be carried out by a usual method which is selected according to the protecting group to be removed, for example, hydrolysis, acid treatment, BBr$_3$ treatment, and catalytic reduction.

The hydrolysis can be carried out by using an inorganic base such as an alkali metal hydroxide (e.g., LiOH, NaOH, and KOH) in a suitable solvent such as ethers (e.g., diethyl ether, dioxane, and THF), alcohols (e.g., MeOH, EtOH), CH₃CN, DMSO, H₂O, and the like at room temperature or with heating.

The acid treatment can be carried out by using an inorganic acid or an organic acid such as hydrochloride, hydrobromide, acetic acid, p-toluenesulfonic acid, and trifluoroacetic acid in a suitable solvent such as ethers (e.g., diethyl ether, dioxane, THF), halogenoalkanes (e.g., CHCl$_3$, CH$_2$Cl$_2$), alcohols (e.g., MeOH, EtOH), CH$_3$CN, DMSO, H$_2$O, and the like at room temperature or with heating.

The catalytic reduction can be carried out by using a catalyst such as palladium on activated carbon and Raney-nickel under a hydrogen atmosphere at room temperature or with heating in a suitable solvent such as ethers (e.g., diethyl ether, dioxane, THF), esters (e.g., methyl acetate, ethyl acetate), alcohols (e.g., MeOH, EtOH), CH$_3$CN, AcOH, H$_2$O, and the like.

The treatment with BBr$_3$ for the demethylation can be carried out in a suitable solvent (e.g., THF, CH$_2$Cl$_2$, AcOH) at a temperature of −78° C. to 50° C.

In case that compound (III-b) wherein R$^1$O is a hydroxyl group is used for the condensation reaction, the hydroxyl group of compound (III-b) should be protected in situ prior to the condensation reaction.

The protection of the hydroxyl group can be carried out by reacting compound (III-b) with a trialkylsilyl halide in a suitable solvent with the presence of a base. Examples of the trialkylsilyl halide include trimethylsilyl chloride, triethylsilyl chloride, and t-butyldimethylsilyl chloride. The base can be selected from conventional bases which are used for the hydroxyl group protection, for example, triethylamine, imidazole, and pyridine. The solvent can be selected from any one which does not disturb the reaction, for example, esters (e.g., methyl acetate, ethyl acetate), aromatic hydrocarbons (e.g., benzene, toluene), halogenoalkanes (e.g., CHCl$_3$, CH$_2$Cl$_2$), ethers (e.g., diethyl ether, THF, DME, dioxane), amides (e.g., DMF, N-methylpyrrolidone), ketones (e.g., acetone, methyl ethyl ketone), CH$_3$CN, DMSO, and a mixture of these solvents. The reaction can be carried out at a temperature of −50° C. to 50° C., preferably from 0° C. to room temperature. The protected compound can be isolated in a usual procedure, if necessary.

Method C:

Among the compounds of the present invention, a compound of formula (I-c):

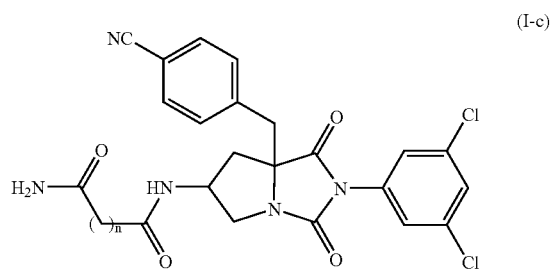

wherein n is the same as defined above, or pharmaceutically acceptable salt thereof, can be prepared by condensing compound (II) with a compound of formula (III-c):

$$H_2NC(=O)-(CH_2)_n N-COOH \qquad (III\text{-}c)$$

wherein n is the same as defined above, a salt thereof, or a reactive derivative thereof, followed by converting the resulting compound into a pharmaceutically acceptable salt thereof, if desired.

The salt of compounds (III-c) may be, for example, a salt with an inorganic base (e.g., an alkali metal salt such as a sodium salt or a potassium salt, an alkaline earth metal salt such as a barium salt or a calcium salt).

The reaction of compound (II) or a salt thereof with compound (III-c) or a salt thereof can be carried out in a similar method as described in Method A.

The starting compound of formula (II) can be prepared in accordance with the description of WO 01/30781 or the following scheme:

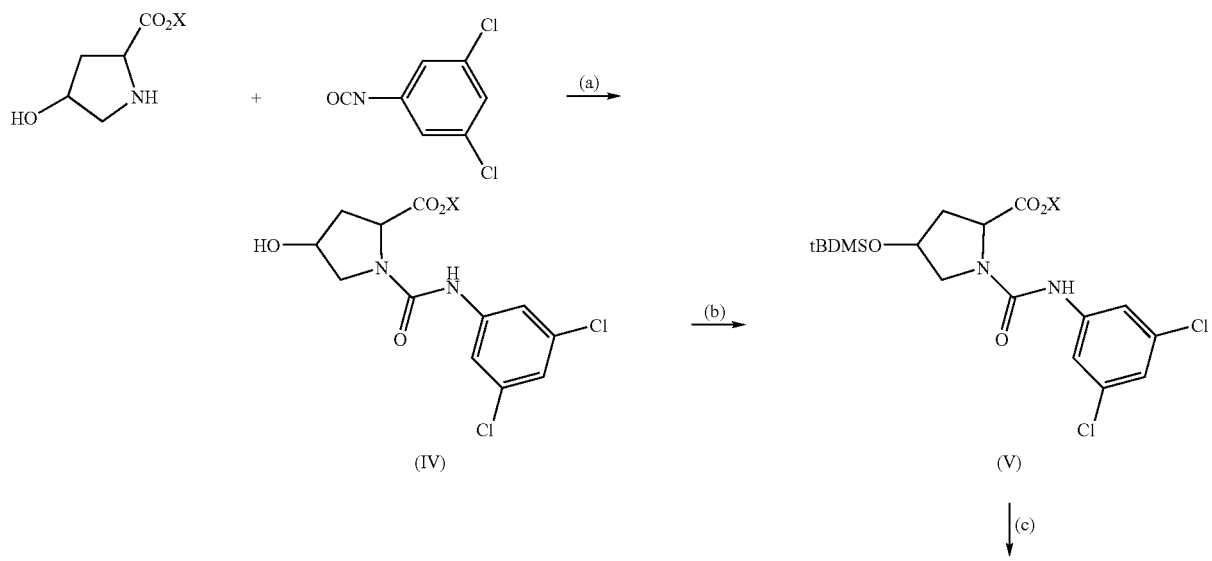

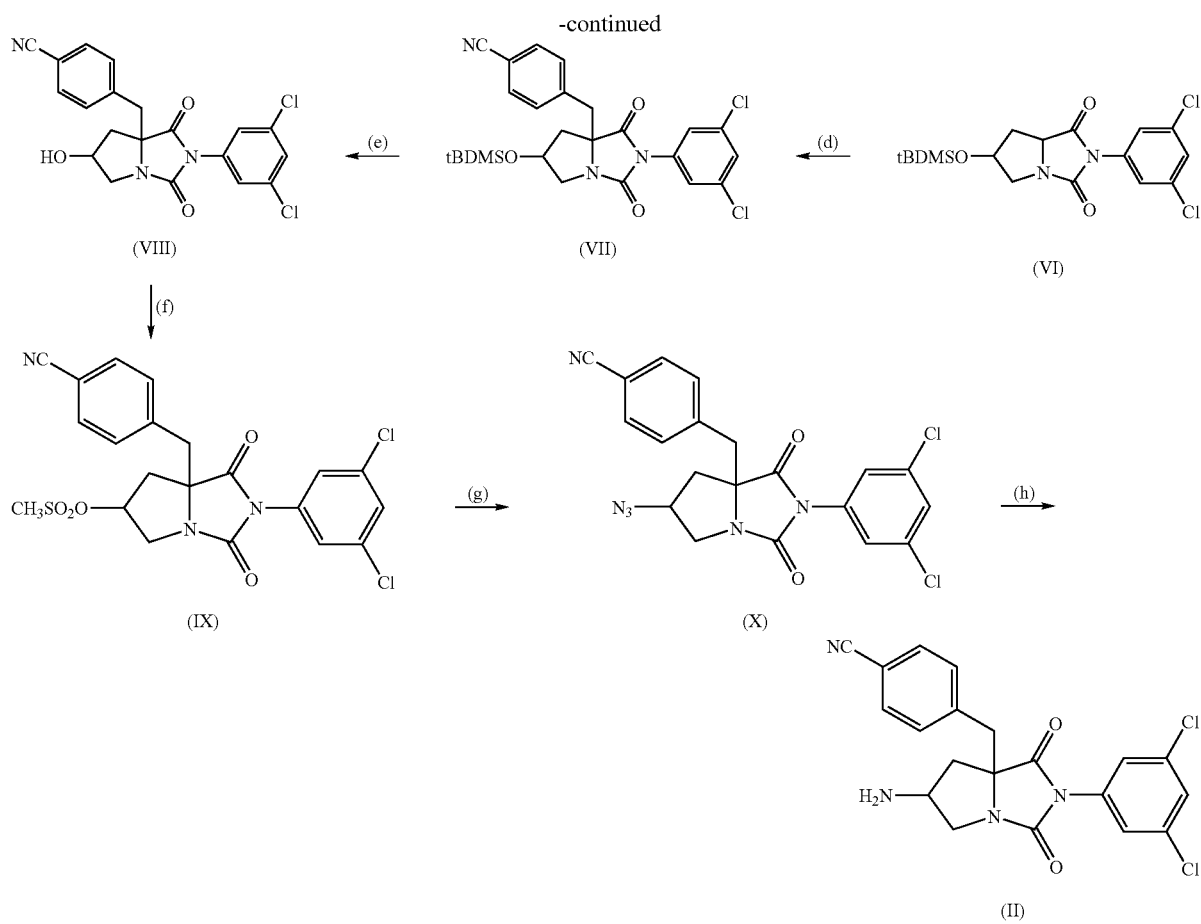

(In the above scheme, X is a $C_{1-6}$ alkyl group or a benzyl group, and tBDMSO is tert-butyldimethylsilyloxy group.)

Step (a): Compound (IV) can be prepared by reacting 4-hydroxyproline $C_{1-6}$ alkyl or benzyl ester with 3,5-dichlorophenylisocyanate in the presence of a base in a suitable solvent.

The base can be selected from conventional organic bases such as an alkylamine (e.g., $Et_3N$, DIEA) and pyridine, and conventional inorganic bases such as an alkali metal hydrocarbonate (e.g., $NaHCO_3$, $KHCO_3$) and an alkali metal carbonate (e.g., $Na_2CO_3$, $K_2CO_3$).

The solvent can be selected from any one which does not disturb the condensation reaction, for example, $CH_2Cl_2$, DME, THF, DMF, HMPA or a mixture thereof. The reaction can be carried out at a temperature of −78° C. to room temperature.

Step (b): Compound (V) can be prepared by protecting the hydroxyl group of compound (IV). The protection can be carried out by a usual manner, for example, by reacting compound (IV) with tert-butyldimethylsilyl chloride in the presence of imidazole in a suitable solvent such as $CH_3CN$. The reaction is carried out at a temperature of 0° C. to boiling point of the solvent, preferably at room temperature.

Step (c): Compound (VI) can be prepared by cyclizing compound (V). The cyclization can be carried out in the presence or absence of a base in a suitable solvent.

The base can be selected from conventional inorganic bases such as an alkali metal alkoxide (e.g., NaOEt, NaOMe), an alkali metal carbonate (e.g., $K_2CO_3$, $Na_2CO_3$) and an alkali metal hydrocarbonate (e.g., $NaHCO_3$), and conventional organic bases such as pyridine, DMAP, $Et_3N$, and DIEA.

The solvent can be selected from any one which does not disturb the cyclization reaction, for example, toluene, DME, $CH_2Cl_2$, THF, $CH_3CN$, DMF, alcohols (e.g., MeOH, EtOH) or a mixture thereof. The reaction is carried out at a temperature of 0° C. to boiling point of the solvent, preferably at 50° C. to 100° C.

Step (d): Compound (VII) can be prepared by condensing compound (VI) with a compound of formula (XI):

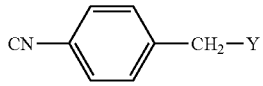

(XI)

wherein Y is a leaving group.

The leaving group may be selected from a halogen atom (e.g., a chlorine atom, a bromine atom, and an iodine atom), p-toluenesulfonyloxy group, and methanesulfonyloxy group.

The condensation reaction can be carried out in the presence of a base in a suitable solvent.

The base can be selected from conventional bases such as an alkali metal amide (e.g., LDA, KHMDS with or without LiCl).

The solvent can be selected from any one which does not disturb the condensation reaction, for example, diethyl ether, DME, THF, DMF, HMPA or a mixture thereof. The reaction can be carried out at a temperature of −78° C. to room temperature.

Step (e): Compound (VIII) can be prepared by deprotecting compound (VII). The deprotection can be carried out by a usual method, for example, treating the compound with HF/pyridine, n-Bu$_4$NF, or an acid (e.g., HCl, AcOH, TFA, p-TsOH) in a suitable solvent or without a solvent.

The solvent can be selected from any one which does not disturb the condensation reaction, for example, CH$_3$CN, THF, DMF alcohols (e.g., MeOH, EtOH) or a mixture thereof. The reaction can be carried out at a temperature of −78° C. to room temperature.

Step (f): Compound (IX) can be prepared by reacting compound (VIII) with methanesulfonyl chloride in the presence of a base in a suitable solvent.

The base can be selected from conventional bases such as Et$_3$N, DIEA, pyridine, NaHCO$_3$, KHCO$_3$, Na$_2$CO$_3$, K$_2$CO$_3$, and KHCO$_3$.

The solvent can be selected from any one which does not disturb the reaction, for example, CH$_2$Cl$_2$, THF, DMF, CH$_3$CN, toluene. The reaction can be carried out at a temperature of −20° C. to 50° C.

Step (g): Compound (X) can be prepared by reacting compound (IX) with an alkali metal azide (e.g., NaN$_3$).

The substitution reaction can be carried out at a temperature of 0° C. to 100° C. in an organic solvent.

The solvent can be selected from any one which does not disturb the reaction, for example, CH$_2$Cl$_2$, THF, DMF, CH$_3$CN, and toluene.

Step (h): Compound (II) can be prepared by reducing compound (X). The reduction can be carried out under catalytic hydrogenation conditions, for example, in the presence of a Pd or Pt catalyst (e.g., Pd—C, PtO$_2$) in a suitable solvent under a H$_2$ atmosphere at room temperature.

The solvent can be selected from any one which does not disturb the reaction, for example, EtOAc, MeOH, and EtOH.

In the present description and the claims, the C$_{1-6}$ alkyl group means a straight chain or branched chain alkyl group having 1 to 6 carbon atoms, for example, methyl group, ethyl group, propyl group, isopropyl group, butyl group, isobutyl group, etc., preferably one having 1 to 4 carbon atoms.

| Abbreviations | |
|---|---|
| AcOEt: | Ethyl acetate (=EtOAc) |
| AcOH: | Acetic acid |
| BOP—Cl: | Bis(2-oxo-3-oxazolidinyl)phosphinic chloride |
| BOP reagent: | Benzotriazol-1-yloxy-tris(dimethylamino)phosphonium hexafluorophosphate |
| BSA: | Bovine serum albumin |
| CDI: | Carbonyldiimidazole |
| DBN: | 1,5-Diazabicyclo[4.3.0]non-5-ene |
| DBU: | 1,8-Diazabicyclo[5.4.0]undec-7-ene |
| DCC: | 1,3-Dicyclohexylcarbodiimide |
| DIEA: | Diisopropylethylamine |
| DMAP: | 4-Dimethylaminopyridine |
| DME: | Dimethoxyethane |
| DMF: | Dimethyl formamide |
| DMSO: | Dimethyl sulfoxide |
| EDC: | 1-(3-Dimethylaminopropyl)-3-ethylcarbodiimide hydrochloride |
| Et: | Ethyl |
| EtOH: | Ethanol |
| HBSS: | Hank's balanced salt solution |
| HMPA: | Hexamethylphosphoramide |
| HOBT: | 1-Hydroxybenzotriazole hydrate |
| HSA: | Human serum albumin |
| KHMDS: | Potassium hexamethyldisilazide (=Potassium bis(trimethylsilyl)amide) |
| LDA: | Lithium diisopropylamide |
| Me: | Methyl |
| MeOH: | Methanol |
| n-Bu: | n-Butyl |
| tBDMS: | tert-Butyldimethylsilyl |
| THF: | Tetrahydrofuran |
| TFA: | Trifluoroacetic acid |
| p-TsOH: | p-toluenesulfonic acid |

EXAMPLES

The compounds of the present invention are exemplified by the following examples but not limited thereby.

Example 1

(5S,7S)-5-(4-Cyanobenzyl)-3-(3,5-dichlorophenyl)-7-acetylamino-1,3-diazabicyclo[3.3.0]octane-2,4-dione To a solution of (5S,7S)-5-(4-cyanobenzyl)-3-(3,5-dichlorophenyl)-7-amino-1,3-diazabicyclo[3.3.0]octane-2,4-dione (78.5 mg) in THF (5 mL) was added acetic anhydride (1.0 mL). The reaction mixture was stirred for 2 hours at 45° C., and the mixture was concentrated and purified by preparative thin-layer chromatography (silica gel; CH$_2$Cl$_2$) to afford the titled compound (84 mg). MS (m/z) 478.8 (MNa$^+$).

Example 2

(5S,7S)-5-(4-Cyanobenzyl)-3-(3,5-dichlorophenyl)-7-[(3-carbamoylpropionyl)amino]-1,3-diazabicyclo[3.3.0]octane-2,4-dione A mixture of (5S,7S)-5-(4-cyanobenzyl)-3-(3,5-dichlorophenyl)-7-amino-1,3-diazabicyclo[3.3.0]octane-2,4-dione (82.7 mg), succinamic acid (45.86 mg), EDC (93.12 mg), HOBT (61.24 mg) and DIEA (104.79 µL) in THF (5 mL) was stirred overnight at room temperature. The reaction mixture was concentrated and purified by high performance liquid chromatography (HPLC) (Beckman 5µ C18 column; eluted with a gradient of H$_2$O/MeCN (10-100%)/0.1% TFA) to give 72 mg of the titled compound. MS (m/z) 536 (MNa$^+$).

Example 3

(5S,7S)-5-(4-Cyanobenzyl)-3-(3,5-dichlorophenyl)-7-[(2-carbamoylacetyl)amino]-1,3-diazabicyclo[3.3.0]octane-2,4-dione A mixture of (5S,7S)-5-(4-cyanobenzyl)-3-(3,5-dichlorophenyl)-7-amino-1,3-diazabicyclo[3.3.0]octane-2,4-dione (200 mg), malonamic acid (59.5 mg), EDC (112 mg), HOBT (97.5 mg) and DIEA (168 µL) in THF (5 mL) was stirred overnight at room temperature. The reaction mixture was evaporated. The residue was dissolved in EtOAc and the resulting solution was washed with water, saturated aqueous NaHCO$_3$ solution, brine, dried (Na$_2$SO$_4$) and concentrated to give 212 mg of the titled compound. MS (m/z) 500 (MH$^+$).

Example 4

(5S,7S)-5-(4-Cyanobenzyl)-3-(3,5-dichlorophenyl)-7-[(3-hydroxypropionyl)amino]-1,3-diazabicyclo[3.3.0]octane-2,4-dione Step 1: A mixture of (5S,7S)-5-(4-cyanobenzyl)-3-(3,5-dichlorophenyl)-7-amino-1,3-diazabicyclo[3.3.0]octane-2,4-dione (0.300 g), 3-methoxypropionic acid (0.209 µL), EDC (0.224 g), HOBT (0.221 g) and DIEA (0.38 µL) in THF (15 mL) was stirred overnight at room temperature. The reaction mixture was evaporated. The residue was purified by HPLC [Beckman 5μ C18 column; eluted with a gradient of H$_2$O/MeCN (10-100%)/0.1% AcOH] to give a foam. It was dissolved in EtOAc and the resulting solution was washed with water, saturated aqueous NaHCO$_3$ solution, brine, dried (Na$_2$SO$_4$) and concentrated to give 0.259 g of (5S,7S)-5-(4-cyanobenzyl)-3-(3,5-dichlorophenyl)-7-[(3-methoxypropionyl)amino]-1,3-diazabicyclo[3.3.0]octane-2,4-dione. MS (m/z) 501 (MH$^+$).

Step 2: BBr$_3$ (3 mL, 1M in CH$_2$Cl$_2$) was added to a solution of (5S,7S)-5-(4-cyanobenzyl)-3-(3,5-dichlorophenyl)-7-[(3-methoxypropionyl)amino]-1,3-diazabicyclo[3.3.0]octane-2,4-dione (0.16 g) in CH$_2$Cl (15 mL) at −78° C. and the mixture was stirred for 8 hours at −78° C. The mixture was evaporated, and the residue was purified by HPLC (Beckman 5μ C18 column; eluted with a gradient of H$_2$O/MeCN (10-100%)/0.1% AcOH) to give foam. It was dissolved in EtoAc and the resulting solution was washed with water, saturated aqueous NaHCO$_3$ solution, brine, dried (Na$_2$SO$_4$) and concentrated to give 0.119 g of the titled compound. MS (m/z) 487 (MH$^+$).

Example 5

(5S,7S)-5-(4-Cyanobenzyl)-3-(3,5-dichlorophenyl)-7-[(2-hydroxyacetyl)amino]-1,3-diazabicyclo[3.3.0]octane-2,4-dione Step 1: To a solution of (5S,7S)-5-(4-cyanobenzyl)-3-(3,5-dichlorophenyl)-7-amino-1,3-diazabicyclo[3.3.0]octane-2,4-dione (150 mg) and DIEA (189 μL) in THF (4 mL) was added a solution of benzyloxyacetyl chloride (57 μL) in THF (2 mL) and the mixture was stirred overnight at room temperature. The reaction mixture was concentrated and the residue was taken up in EtOAc. The resulting solution was washed with brine, dried (Na$_2$SO$_4$), filtered and concentrated. The residue was purified by HPLC (Beckman 5μ C18 column; eluted with a gradient of H$_2$O/MeCN (10-100%)/0.1% AcOH) to give a foam. It was dissolved in EtOAc and the resulting solution was washed with water, saturated aqueous NaHCO$_3$ solution, brine, dried (Na$_2$SO$_4$) and concentrated to give 0 135 g of (5S,7S)-5-(4-cyanobenzyl)-3-(3,5-dichlorophenyl)-7-[(2-benzyloxyacetyl)amino]-1,3-diazabicyclo[3.3.0]octane-2,4-dione. MS (m/z) 563.4 [MH$^+$].

Step 2: Hydrogen was bubbled through a solution of (5S,7S)-5-(4-cyanobenzyl)-3-(3,5-dichlorophenyl)-7-[(2-benzyloxyacetyl)amino]-1,3-diazabicyclo[3.3.0]octane-2,4-dione from step 1 (0.125 g) in EtOH (10 mL) containing Pd/C (5%, 15 mg) and the reaction mixture was stirred overnight under a H$_2$ atmosphere. The mixture was recharged with additional 5% Pd/C (10 mg) and stirred overnight under a H$_2$ atmosphere. The reaction mixture was filtered through a bed of Celite and the filtrate was concentrated. The residue was purified by HPLC (Beckman 5μ C18 column; eluted with a gradient of H$_2$O/MeCN (10-100%)/0.1% TFA) to give 0.023 g of the titled compound. MS (m/z) 473 [MH$^+$] and 495 [MNa+].

Reference Example 1

(5S,7S)-5-(4-Cyanobenzyl)-3-(3,5-dichlorophenyl)-7-amino-1,3-diazabicyclo[3.3.0]octane-2,4-dione The titled compound was prepared in accordance with the following scheme:

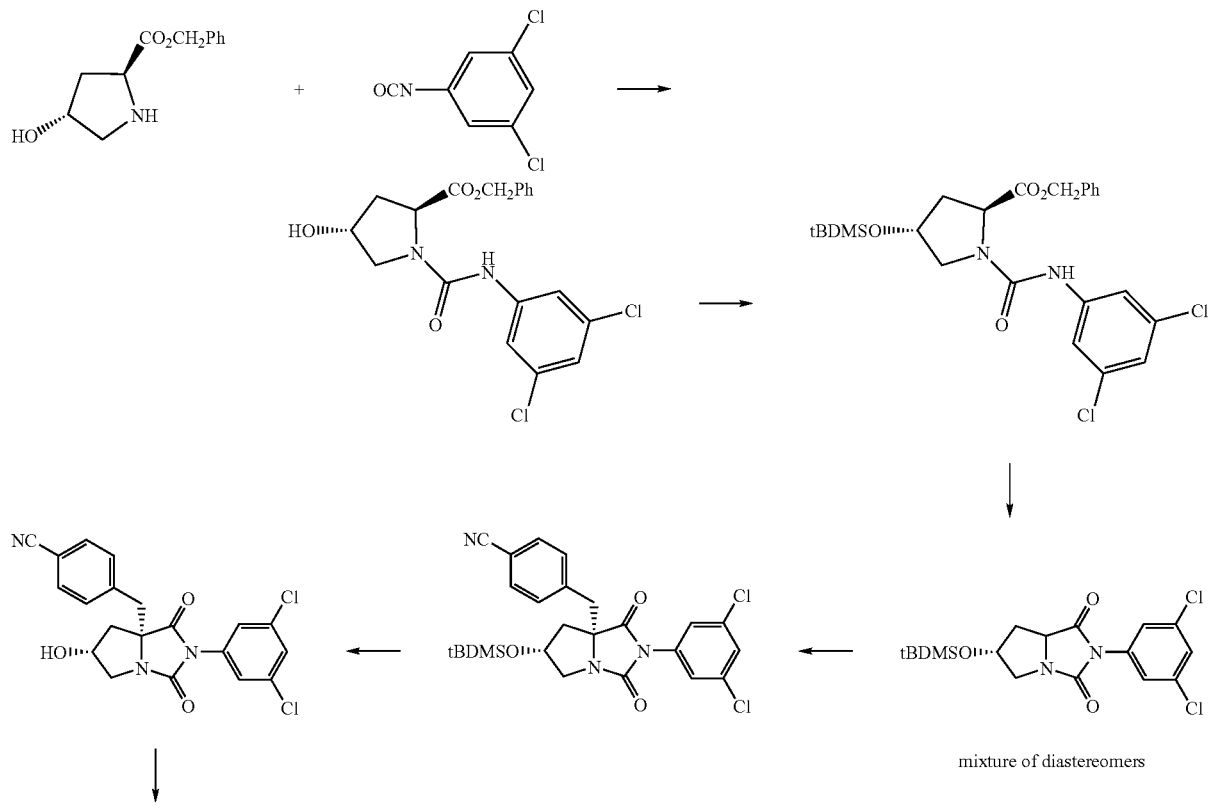

Scheme 2 mixture of diastereomers

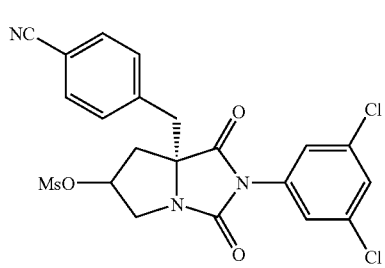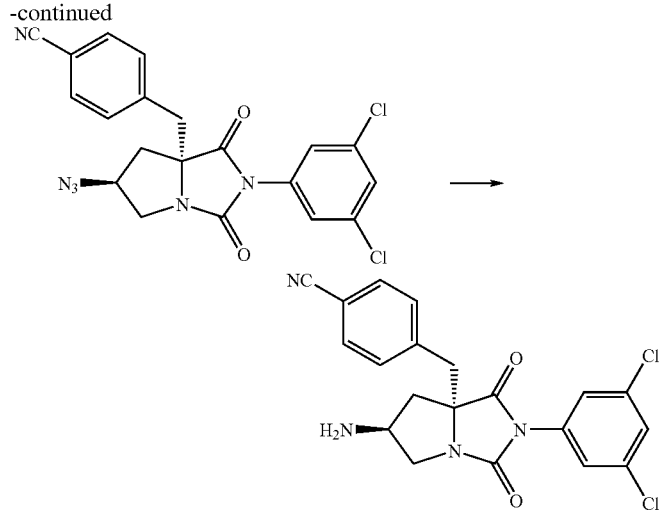

(In the above scheme, tBDMSO is tert-butyldimethylsilyloxy group, and MsO is methanesulonyloxy group.)

Step-1: p-Toluene sulfonic acid (50.6 g) was added to a suspension of L-4-trans-hydroxyproline (25.25 g) in a mixture of benzyl alcohol (100 mL) and benzene (250 mL) and the mixture was heated under a Dean Stark trap for 24 hours. The reaction mixture was concentrated and diethyl ether was added to precipitate the solid. The solid was filtered, washed with additional diethyl ether and dried to yield 75 g of L-4-trans-hydroxyproline benzyl ester.

Step-2: To a suspension of L-4-trans-hydroxyproline benzyl ester p-toluene sulfonic acid salt from step 1 (40.43 g) in THF (500 mL) and DIEA (51.3 mL) was added 3,5-dichlorophenylisocyanate (22.1 g). After stirring overnight, the reaction mixture was concentrated. The residue was dissolved in EtOAc, washed with 0.5 N HCl, saturated aqueous NaHCO$_3$ solution, brine, dried (Na$_2$SO$_4$), filtered and concentrated. The residue was triturated in EtOAc/hexane (1:1) and the white solid was filtered and purified via flash column chromatography (silica gel; hexane/EtOAc 2:1) to yield (2S,4R)-2-[(3,5-dichlorophenyl)carbamoyl]-4-hydroxyproline benzyl ester (33.07 g).

Step-3: To a suspension of (2S,4R)-2-[(3,5-dichlorophenyl)carbamoyl]-4-hydroxyproline benzyl ester (33.07 g) in CH$_3$CN (800 mL) was added imidazole (11 g) and tert-butyldimethylsilyl chloride (13.64 g). After stirring for 48 hours, the reaction mixture was concentrated. The residue was dissolved in EtOAc, washed with 0.5 N HCl, saturated aqueous NaHCO$_3$ solution, brine, dried (Na$_2$SO$_4$), filtered and concentrated. The residue was purified via flash column chromatography (silica gel; hexane/EtOAc 2:1) to give (2S,4R)-2-[(3,5-dichlorophenyl)carbamoyl]-4-(tert-butyldimethylsilyloxy)proline benzyl ester (44.45 g).

Step-4: To a solution of the (2S,4R)-2-[(3,5-dichlorophenyl)carbamoyl]-4-(tert-butyldimethylsilyloxy)proline benzyl ester (23.49 g) in CH$_3$CN (500 mL) was added DIEA (34.44 mL) and the mixture was heated to reflux. After refluxing for 24 hours the reaction mixture was concentrated and purified by flash column chromatography (silica gel; hexane to hexane/EtOAc 1:1) to separate the two diastereomers of 3-(3,5-dichlorophenyl)-7-(tert-butyldimethylsilyloxy)-1,3-diazabicyclo[3.3.0]octane-2,4-dione. Diastereomer A: 7.46 g, MS: m/z 415 (M+); and Diastereomer B: 10.66 g, MS: m/z 415 (M+).

Step-5: The compound from step 4, diastereomer A or B, (12.73 g) was benzylated as follows. n-Butyl lithium (30 mL, 1.6 M in hexane) was added with stirring to a solution of diisopropylamine (6.5 mL) in THF (100 mL) at −78° C. under a N$_2$ atmosphere. The mixture was maintained at that temperature for additional 30 minutes. The mixture was added via cannula to a solution of 3-(3,5-dichlorophenyl)-7-(tert-butyldimethylsilyloxy)-1,3-diazabicyclo[3.3.0]octane-2,4-dione (12.73 g) in dry THF (100 mL) at −78° C. under a N$_2$ atmosphere. After stirring at −78° C. for 30 minutes, 4-cyano-α-bromotoluene (9.08 g) in THF (100 mL) was added. The reaction mixture was stirred at −78° C. for 2.5 hours, then slowly warmed up to room temperature and allowed to stand at room temperature for 0.5 hour. The reaction mixture was concentrated and the residue was dissolved in EtOAc. The EtOAc solution was washed with 0.5 N HCl, saturated aqueous NaHCO$_3$ solution, brine, dried (Na$_2$SO$_4$), filtered and concentrated. The residue was purified via flash column chromatography (silica gel; hexane/EtOAc 24:1 to 3:1) to give (5S,7R)- and (5R,7R)-5-(4-cyanobenzyl)-3-(3,5-dichlorophenyl)-7-(tert-butyldimethylsilyloxy)-1,3-diazabicyclo[3.3.0]octane-2,4-dione.

(5S,7R) isomer: 7.6 g, MS: m/z 530 (M+); and
(5R,7R) isomer: 1.8 g, MS: m/z 530 (M+)

Step-6: To a solution of (5S,7R)-5-(4-cyanobenzyl)-3-(3,5-dichlorophenyl)-7-(tert-butyldimethylsilyloxy)-1,3-diazabicyclo[3.3.0]octane-2,4-dione (1.0 g) in THF (1 mL) was added 70% HF/pyridine (25 mL). The reaction mixture was stirred for 24 hours and then evaporated. The residue was dissolved in EtOAc and the resulting solution was washed with water, saturated aqueous NaHCO$_3$ solution, brine, dried (Na$_2$SO$_4$) and concentrated. The residue was purified by flash column chromatography (silica gel; MeOH/CH$_2$Cl$_2$ 2-7%) to give (5S,7R)-5-(4-cyanobenzyl)-3-(3,5-dichlorophenyl)-7-hydroxy-1,3-diazabicyclo[3.3.0]octane-2,4-dione (0.52 g). MS (m/z) 416 [MH$^+$].

Step 7: To a solution of (5S,7R)-5-(4-cyanobenzyl)-3-(3,5-dichlorophenyl)-7-hydroxy-1,3-diazabicyclo[3.3.0]octane-2,4-dione from step 6 (0.52 g) in CH$_2$Cl$_2$ (8 mL) at 0° C. was added DIEA (0.45 mL) followed by methanesulfonyl chloride (0.15 mL) and the mixture stirred for 1.5 hours. The reaction mixture was diluted with CH$_2$Cl$_2$ and the resulting mixture was washed with saturated aqueous NaHCO$_3$ solution followed by brine, dried (Na$_2$SO$_4$), filtered and concentrated to give 0.76 g of (5S,7R)-5-(4- cyanobenzyl)-3-(3,5-dichlorophenyl)-7-methanesulfonyloxy-1,3-diazabicyclo[3.3.0]octane-2,4-dione. This compound was used as is for the next step. MS (m/z) 501 [MH⁺].

Step 8: NaN₃ was added to a solution of (5S,7R)-5-(4-cyanobenzyl)-3-(3,5-dichlorophenyl)-7-methanesulfonyloxy-1,3-diazabicyclo[3.3.0]octane-2,4-dione from step 7 (0.76 g) in DMF (5 mL) and the mixture was stirred for 24 hours. The reaction mixture was partitioned between EtOAc and water. The organic solution was washed with brine, dried (Na₂SO₄), filtered and concentrated. The residue was purified by flash column chromatography (silica gel; CH₂Cl₂) to give 0.46 g of (5S, 7S)-5-(4-cyanobenzyl)-3-(3,5-dichlorophenyl)-7-azido-1,3-diazabicyclo[3.3.0]octane-2,4-dione. MS (m/z) 441 [MH⁺].

Step 9: Hydrogen was bubbled through a solution of (5S, 7S)-5-(4-cyanobenzyl)-3-(3,5-dichlorophenyl)-7-azido-1, 3-diazabicyclo[3.3.0]octane-2,4-dione from step 8 (0.42 g) in EtOH (15 mL) containing Pd/C (5%, 15 mg) and the reaction mixture was stirred overnight under a H₂ atmosphere. The reaction mixture was filtered through a bed of Celite and the filtrate was concentrated. The residue was purified by HPLC (Beckman 5μ C18 column; eluted with a gradient of H₂O/MeCN (10-100%)/0.1% TFA) to give 0.21 g of (5S,7S)-5-(4-cyanobenzyl)-3-(3,5-dichlorophenyl)-7-amino-1,3-diazabicyclo[3.3.0]octane-2,4-dione. MS (m/z) 415 [MH⁺].

Reference Example 2

(5S,7S)-5-(4-Cyanobenzyl)-3-(3,5-dichlorophenyl)-7-amino-1,3-diazabicyclo[3.3.0]octane-2,4-dione Step 1: 3-(3,5-Dichlorophenyl)-7-(tert-butyldimethylsilyloxy)-1,3-diazabicyclo[3.3.0]octane-2,4-dione was prepared by following similar procedures as described in Reference Example 1, steps 1 through 4, but replacing L-4-trans-hydroxyproline benzyl ester p-toluene sulfonic acid salt with L-4-trans-hydroxyproline methyl ester hydrochloride.

Step 2: 3-(3,5-Dichlorophenyl)-7-(tert-butyldimethylsilyloxy)-1,3-diazabicyclo[3.3.0]octane-2,4-dione from step 1 was treated in similar procedures as described in Reference Example 1, steps 5 through 9 to afford the titled compound.

Cell Adhesion Protocol

Cell Adhesion The recombinant protein ICAM-1•Fc was constructed from the 5 extracellular domains of human ICAM-1 and fusion with the constant region of human IgG. ICAM-1•Fc was purified by Protein A affinity chromatography and stored in aliquots at −20° C. Immobilized ICAM-1•Fc was prepared by dilution of the protein in PBS pH 7.5, transfer of 100 μl/well to Falcon Probind III plates and overnight incubation at 4° C. Wells coated with BSA served as a measure of non-specific background adhesion. Washed plates were blocked with a solution of 0.25% ovalbumin in PBS for 1 h at 37° C. HBSS washed Jurkat cells were suspended to a final concentration of 2.5×10⁶/ml in TBSg adhesion buffer (24 mM Tris pH 7.4, 0.14 M NaCl, 2.7 mM KCl, 2 mM glucose, 0.1% HSA). A 100 μl volume of cells was added to the blocked and washed ICAM-1•Fc coated plates that contained 100 μl of plate buffer (TBSg, 10 mM MgCl₂, 2% DMSO). Adhesion was for 1 h at 37° C. Non-adherent cells were removed using the EL404 plate washer (BioTek Instruments; Highland Park, Vt.). The number of adherent cells was quantified by measuring enzymatic activity of endogenous N-acetyl-hexosaminidase using the enzyme substrate p-nitrophenol-N-acetyl-β-D-glucoseaminide, pNAG. The amount of liberated p-nitrophenol was measured by reading the optical density at 405 nm using a vertical pathway spectrophotometer to quantify cell attachment (VMAX Kinetic Microplate Reader, Molecular Devices, Menlo Park, Calif.). For competition studies the compounds from 100% DMSO stock solutions were diluted in plate buffer at 2-fold the required testing concentration prior to transfer to the ICAM-1•Fc coated plate and serial dilution.

The invevtion claimed is:

1. A compound of the formula (I):

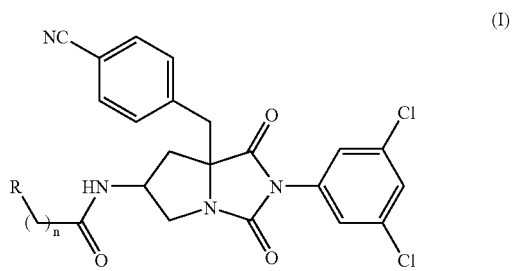

(I)

wherein R is hydrogen atom, hydroxyl group or carbamoyl group, and n is 1 or 2, or a pharmaceutically acceptable salt thereof.

2. The compound or salt according to claim 1, wherein R is hydrogen atom.

3. The compound or salt according to claim 1, wherein R is hydroxyl group.

4. The compound or salt according to claim 1, wherein R is carbamoyl group.

5. The compound or salt according to any one of claims 1-4, wherein n is 1.

6. The compound or salt according to any one of claims 1-4, wherein n is 2.

7. The compound or salt according to claim 1, wherein R is hydrogen atom and n is 1.

8. The compound or salt according to claim 1, wherein R is hydroxyl group and n is 1.

9. The compound or salt according to claim 1, wherein R is carbamoyl group and n is 2.

10. The compound or salt according to claim 1, wherein the compound is selected from the following compounds:
    (5S, 7S)-5-(4-Cyanobenzyl)-3-(3,5-dichlorophenyl)-7-acetylamino-1,3-diazabicyclo[3.3.0]octane-2,4-dione,
    (5S, 7S)-5-(4-Cyanobenzyl)-3-(3,5-dichlorophenyl)-7-[(2-hydroxyacetyl)amino]-1,3-diazabicyclo[3.3.0]octane-2,4-dione,
    (5S, 7S)-5-(4-Cyanobenzyl)-3-(3,5-dichlorophenyl)-7-[(3-carbamoylpropionyl)amino]-1,3-diazabicyclo[3.3.0]octane-2,4-dione.

11. A process for preparing a compound of formula (I-a):

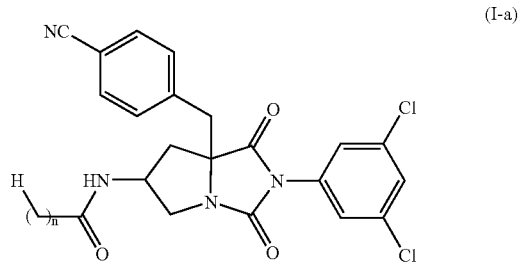

(I-a)

wherein n is 1 or 2, or a pharmaceutically acceptable salt thereof, which comprises condensing a compound of formula (II):

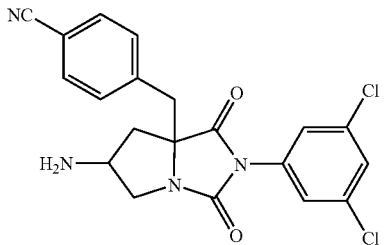
(II)

or a salt thereof, with a compound of formula (III-a):

H—(CH$_2$)$_n$—COOH  (III-a)

wherein n is the same as defined above, a salt thereof or a reactive derivative thereof selected from the group consisting of an acid halide, a reactive ester, an anhydride thereof, and mixed anhydride with other carboxylic acid, followed by converting the resulting compound into a pharmaceutically acceptable salt thereof, if desired.

12. A process for preparing a compound of formula (I-b):

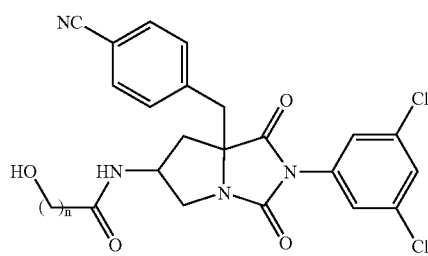
(I-b)

wherein n is 1 or 2, or a pharmaceutically acceptable salt thereof, which comprises condensing a compound of formula (II):

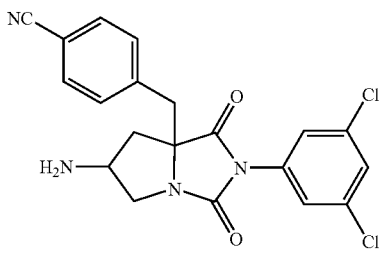
(II)

or a salt thereof, with a compound of formula (III-b):

R$^1$O—(CH$_2$)$_n$—COOH  (III-b)

wherein R$^1$O is a protected or unprotected hydroxyl group, and n is the same as defined above, a salt thereof or a reactive derivative thereof selected from the group consisting of an acid halide, a reactive ester, an anhydride thereof, and mixed anhydride with other carboxylic acid, followed by removing the protecting group, and further converting the resulting compound into a pharmaceutically acceptable salt thereof, if necessary.

13. A process for preparing a compound of formula (I-c):

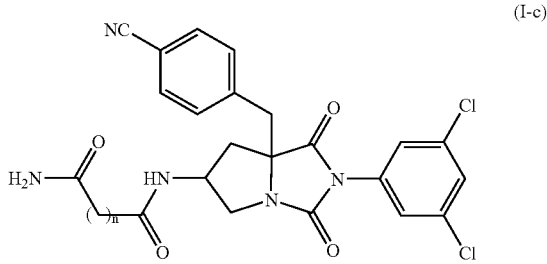
(I-c)

wherein n is 1 or 2, or a pharmaceutically acceptable salt thereof, which comprises condensing a compound of formula (II)

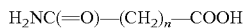
(II)

or a salt thereof, with a compound of formula (III-c):

H$_2$NC(=O)—(CH$_2$)$_n$—COOH  (III-c)

wherein n is the same as defined above, a salt thereof or a reactive derivative thereof selected from the group consisting of an acid halide, a reactive ester, an anhydride thereof, and mixed anhydride with other carboxylic acid, followed by converting the resulting compound into a pharmaceutically acceptable salt thereof, if desired.

14. A pharmaceutical composition which comprises a therapeutically effective amount of the compound or salt as set forth in claim 1 in admixture with a therapeutically acceptable carrier or diluent.

* * * * *